US010076618B2

(12) United States Patent
Ahearn et al.

(10) Patent No.: US 10,076,618 B2
(45) Date of Patent: Sep. 18, 2018

(54) NITROUS OXIDE SAFETY SYSTEM

(76) Inventors: David J. Ahearn, Little Compton, RI (US); Edward Carey, Westport, MA (US)

(*) Notice: Subject to any disclaimer, the term of this patent is extended or adjusted under 35 U.S.C. 154(b) by 1672 days.

(21) Appl. No.: 12/398,783

(22) Filed: Mar. 5, 2009

(65) Prior Publication Data

US 2009/0223567 A1 Sep. 10, 2009

Related U.S. Application Data

(60) Provisional application No. 61/034,071, filed on Mar. 5, 2008.

(51) Int. Cl.
*A61M 16/00* (2006.01)
*A61M 16/10* (2006.01)

(52) U.S. Cl.
CPC ......... *A61M 16/009* (2013.01); *A61M 16/104* (2013.01); *A61M 2202/0208* (2013.01); *A61M 2202/0283* (2013.01); *Y02C 20/10* (2013.01); *Y10T 137/0379* (2015.04); *Y10T 137/7837* (2015.04)

(58) Field of Classification Search
CPC ........... F16K 17/36; A61M 2202/0208; A61M 16/104; A61M 2202/0283; A61M 16/009; Y02C 20/10; C02F 1/763; G05D 16/0619; G05D 23/1313; G05D 11/132; G05D 11/006; A01C 23/04
USPC ........ 128/203.14, 205.24; 137/87.01, 88, 93, 137/12, 511
See application file for complete search history.

(56) References Cited

U.S. PATENT DOCUMENTS

| 3,206,159 | A | * | 9/1965 | Anderson et al. .............. 251/28 |
| 3,360,007 | A |  | 12/1967 | Haidek |
| 3,662,774 | A |  | 5/1972 | Johannisson et al. |
| 3,800,793 | A |  | 4/1974 | Marrese et al. |
| 4,026,284 | A |  | 5/1977 | Boehringer |

(Continued)

FOREIGN PATENT DOCUMENTS

JP 59172019 9/1984

OTHER PUBLICATIONS

"Porter Nitrous Oxide Sedation Systems AVS Automatic Switch", Aug. 2003, Porter Instrument Company.*

(Continued)

*Primary Examiner* — Chee-Chong Lee
(74) *Attorney, Agent, or Firm* — Adler Pollock & Sheehan P.C.; Daniel J. Holmander, Esq.

(57) ABSTRACT

The present invention is a nitrous oxide safety system or method that provides a safety control valve actuated by low-vacuum fluids to control the release of nitrous oxide therethrough. The nitrous oxide safety system may include a low-vacuum fluid, a nitrous oxide fluid, a scavenging mask assembly, and a safety control valve. The low-vacuum fluid is generated by a vacuum source operating to achieve a predetermined parameter and the nitrous oxide fluid is provided by a nitrous oxide source. The scavenging mask assembly is fluidly connected with the nitrous oxide source and the vacuum source. The safety control valve is fluidly connected to the fluid connection between the nitrous oxide source and the vacuum source. The safety control valve is configured to be actuated when the low-vacuum fluid is input to the valve to release a flow of the nitrous oxide fluid through the safety control valve.

2 Claims, 3 Drawing Sheets

(56) References Cited

U.S. PATENT DOCUMENTS

| | | | |
|---|---|---|---|
| 4,143,850 A * | 3/1979 | Brakebill | 251/28 |
| 4,180,066 A | 12/1979 | Milliken et al. | |
| 4,215,409 A | 7/1980 | Strowe | |
| 5,568,910 A | 10/1996 | Koehler et al. | |
| 6,202,645 B1 | 3/2001 | Brown | |
| 6,305,375 B1 * | 10/2001 | Brown | 128/205.24 |
| 6,679,259 B2 | 1/2004 | Heesch | |
| 6,712,095 B2 | 3/2004 | Williamson et al. | |
| 7,243,649 B2 | 7/2007 | Moenning et al. | |
| 2001/0020471 A1 | 9/2001 | Kitten | |

OTHER PUBLICATIONS

"MXR Flowmeter User's Manual", Oct. 2006, Parker Hannifin Corporation, pp. 9-10, 12.*

Porter Instrument Company, "Porter Nitrous Oxide Sedation Systems", Feb. 2005, Porter Instrument Company Inc., FM-1046 Rev. 0.2/05, pp. 1-15.*

"Controlling Exposures to Nitrous Oxide During Anesthetic Administration", DHHS (NIOSH) Publication No. 94-100, Aug. 5, 1996.

Porter Instrument, General Sedation, http://www.porterinstrument.com/pdfs/General Sedation.pdf, Mar. 2007.

Center for Disease Control, US Department of Health and Human Services: Case Study E "Dental Administration of Nitrous Oxide Safety System"—Aug. 1992, p. 47-50.

* cited by examiner

NITROUS OXIDE SAFETY SYSTEM

CROSS REFERENCE TO RELATED APPLICATION

This application is related to and claims priority from earlier filed provisional patent application Ser. No. 61/034,071, filed Mar. 5, 2008 and incorporated herein by reference.

BACKGROUND OF THE INVENTION

The present invention relates to a method or system of controlling fluid flow. More particularly, the present invention relates to a nitrous oxide safety method or system which provides a safety control valve actuated by low-vacuum fluids to control the release of nitrous oxide therethrough.

Pneumatically-actuated on/off or control valves which open and close are known in the art. Such valves may include, for example, a piloted actuator which is opened and closed by a pneumatic, vacuum control fluid source which is connected to an input port on the valve. Movement of the piloted actuator is caused by a pressure differential created across the actuator by the control fluid.

Movement of the actuator may be used to perform a wide variety of functions. For example, movement of the actuator may control the flow of a second fluid source which is connected to a second input port on the valve. This type of valve acts as a monitor by responding to the vacuum input of the control fluid and then acts as a controller to actuate and/or control the flow of the second fluid through the valve.

Many applications require a pneumatically-actuated valve which is responsive to the input of a low vacuum pressure control fluid. As used herein, "low vacuum" is used to refer to vacuum strengths of 2-20 inches Hg, though performance within this range can be selected via design parameters. It should be understood that in a system with fixed conduit and orifice sizes, flow rate is proportional to vacuum strength levels.

In the dental field, the vacuum fluid is generated by an industrial vacuum system which services the individual devices within the dental operatory suites. For instance, these devices may include high volume oral evacuators, saliva ejectors, surgical suction and Nitrous Oxide (N2O) scavenging systems.

With a scavenging system, the mixture of gases, from excess input and exhalation, is suctioned from the mask by a vacuum source which is connected to and manually controlled by an on/off valve. These scavenged gases are safely exhausted outside of the operatory suite. NIOSH Alert 94-100 Controlling Exposure to Nitrous Oxide During Anesthetic Administration 1994 recommends a minimum flow rate of 45 liters per minute for vacuum scavenging systems.

In dental anesthesia/analgesia applications, it is critical that the vacuum source be activated and functioning properly at any time a supply of anesthesia/analgesia gas is delivered to the patient. If excess anesthesia/analgesia gas and exhalation gases from the patient are not scavenged by the vacuum source, a potentially hazardous condition builds up in the treatment room. In prior art anesthesia/analgesia configurations, the vacuum source is activated by a manual control valve which must be opened by an operator independently from the valve controlling the flow of anesthesia/analgesia gas.

A dangerous situation can exist where anesthesia/analgesia gas can be flowing without vacuum scavenging systems functioning. This could happen because of human error where the operator forgets to activate the vacuum scavenging system at the beginning of a procedure. Or, the operator could turn off the vacuum scavenging system and fail to properly turn off the anesthesia/analgesia gas at the end of a procedure. Also, it could occur due to a mechanical failure or overloading of the vacuum system, which is undetected by the operator, while anesthesia/analgesia gas is flowing.

Therefore, it would be particularly desirable to provide a system or method for nitrous oxide which provides a safety control valve actuated by low-vacuum fluids to control the release of nitrous oxide therethrough. Currently, there is no system in the prior art, used to safely control nitrous oxide flow proportional to the vacuum level.

BRIEF SUMMARY OF THE INVENTION

An embodiment of the present invention preserves the advantages of prior art nitrous oxide safety systems or methods. In addition, it provides new advantages not found in currently available nitrous oxide safety systems or methods and overcomes many disadvantages of such currently available nitrous oxide safety systems or methods.

The present invention is a nitrous oxide safety system or method which provides a safety control valve actuated by low-vacuum fluids to control the release of nitrous oxide therethrough. The nitrous oxide safety system may include a low-vacuum fluid, a nitrous oxide fluid provided by a nitrous oxide source, a scavenging mask, and a safety control valve, preferably a vacuum actuated valve.

The low-vacuum fluid is generated by a vacuum source operating to achieve a predetermined parameter. For example, a parameter of the vacuum source is a vacuum strength of 2-20 inches of Hg. In another example, the parameter of the vacuum source is maintaining a scavenging flow rate of at least 45 L/min at the scavenging mask.

The scavenging mask is fluidly connected with the nitrous oxide source and the vacuum source. The safety control valve is connected to the fluid connection between the nitrous oxide source and the vacuum source. The safety control valve is defaulted to be closed until predetermined parameter of the vacuum source is attained to provide said low-vacuum fluid. If necessary, the safety control valve is configured to provide a user the ability to manually open the safety control valve. In a further embodiment, the safety control valve is a variable safety control valve configured for adjusting the predetermined parameter for the vacuum source to release the nitrous oxide.

In operation, the safety control valve is configured to be actuated when the low-vacuum fluid generated by a vacuum source operating a predetermined parameter is input within the valve to release a flow of the nitrous oxide fluid through the safety control valve. The safety control valve is configured to automatically shut off flow of said nitrous oxide when vacuum source is operating below the predetermined parameter. Also, the safety control valve may be configured to automatically shut off flow of the nitrous oxide when flow rate of vacuum source is operating below the flow rate of said nitrous oxide. In one embodiment, the safety control valve is a vacuum actuated valve or a pneumatically-actuated valve.

The present invention method also provides a method for controlling nitrous oxide including the following steps. First step, a low-vacuum fluid is generated by a vacuum source operating to achieve a predetermined parameter. Second step, a nitrous oxide fluid is provided from a nitrous oxide source. Fourth step, a means for scavenging excess nitrous oxide in fluid connection with the nitrous oxide source and the vacuum source is provided. Fifth step, a safety control valve is connected to the fluid connection between the nitrous oxide source and the vacuum source. The safety control valve configured to be actuated when the low-vacuum fluid generated by the vacuum source is operating to achieve the predetermined parameter is input within the valve to release a flow of the nitrous oxide fluid. Sixth step, the means for scavenging excess nitrous oxide is provided to connect to the vacuum source and the nitrous oxide source onto a patient. Seventh step, the flow rate, strength, or both of the vacuum source is increased to provide low-vacuum fluid into said safety control valve. Eighth step, nitrous oxide is released through the safety control valve upon the vacuum source reaching a predetermined rate. Ninth step, excess nitrous oxide is retrieved from the means for scavenging excess nitrous oxide using the vacuum source. Tenth step, the vacuum source is decreased below the predetermined flow rate, strength, or both which prevents the safety control valve from releasing nitrous oxide. Overall, the method for controlling nitrous oxide provides a safety control valve actuated by low-vacuum fluids to control a release of nitrous oxide therethrough.

It is therefore an object of the present invention to provide a method or system for a nitrous oxide safety system which provides a safety control valve actuated by low-vacuum fluids to control the release of nitrous oxide through the safety control valve.

It is a further object of the present invention to have the vacuum source operating any time during delivery of nitrous oxide to a patient.

It is also an object of the present invention to prevent build up of nitrous oxide gas at dangerous levels in a medical or dental office.

Another object of the present invention is to reduce human error of not operating a vacuum source during release of nitrous oxide in a medical or dental office.

Furthermore, another object of the present is to provide greater safety to patients and medical or dental persons during release of nitrous oxide in a medical or dental office.

Other objects, features and advantages of the invention shall become apparent as the description thereof proceeds when considered in connection with the accompanying illustrative drawings.

BRIEF DESCRIPTION OF THE DRAWINGS

The novel features which are characteristic of the nitrous oxide safety systems and methods are set forth in the appended claims. However, the nitrous oxide safety systems and methods, together with further embodiments and attendant advantages, will be best understood by reference to the following detailed description taken in connection with the accompanying drawings in which:

DETAILED DESCRIPTION OF PREFERRED EMBODIMENTS

Figure 1:
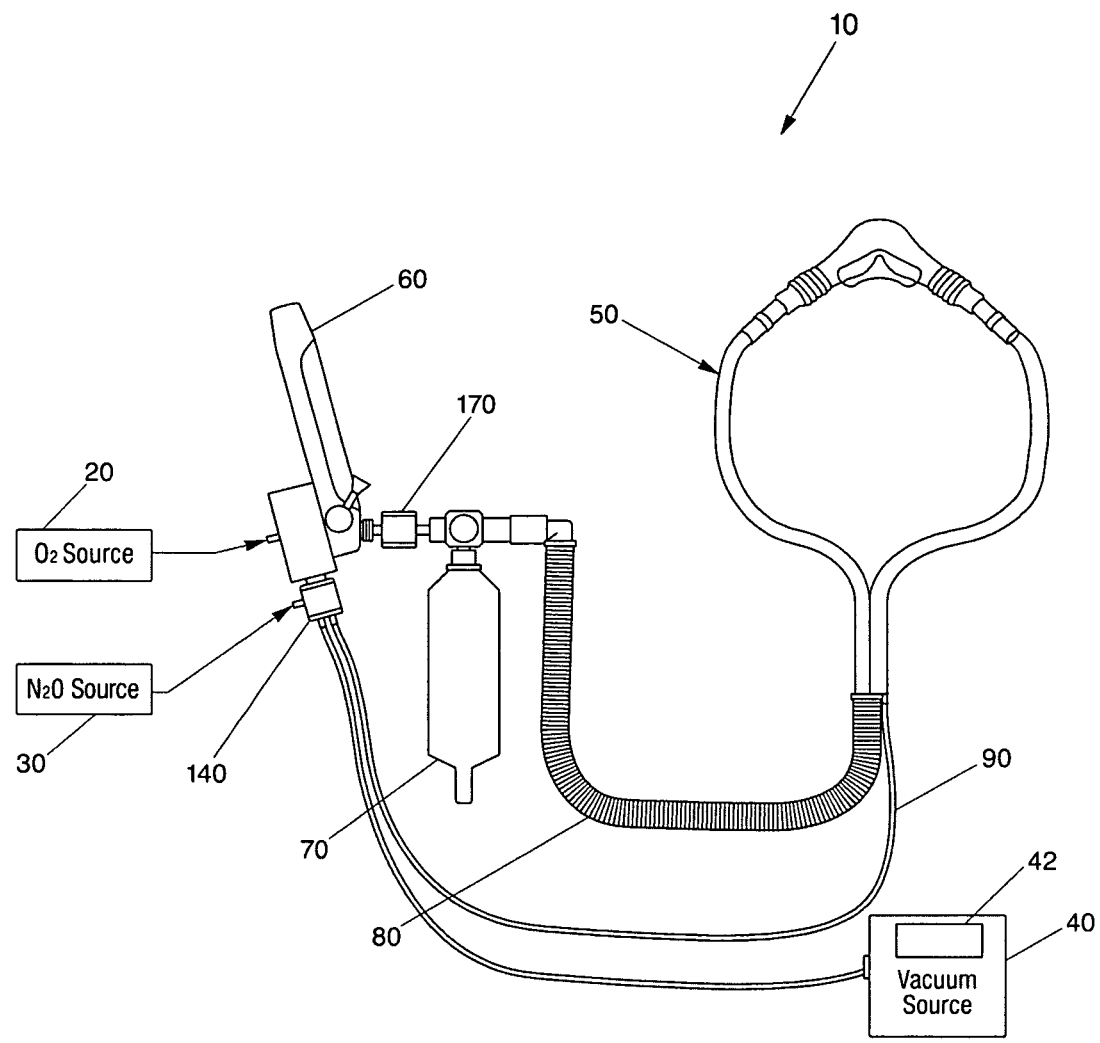
FIG. 1 is a nitrous oxide safety system including a safety control valve of the present invention.

Referring to FIG. 1, a nitrous oxide safety system 10 of the present invention is shown. The present invention is a nitrous oxide safety system 10 or method which provides a safety control valve 140, preferably vacuum actuated valve, actuated by low-vacuum fluids to control a release of nitrous oxide therethrough. The nitrous oxide safety system may include a low-vacuum fluid generated by a vacuum source 40, a nitrous oxide fluid provided by a nitrous oxide source 30, a scavenging mask 50, and a safety control valve 140. In addition, the nitrous oxide safety system 10 may also include an oxygen source 20, mixing valve 170, flow meter 60, breathing bag 70, and tubing 80, 90 or lines. Note, the nitrous oxide safety system 10 of the present invention may include elements of the system disclosed in "Nitrous Oxide Anaesthetic Administration System" (Provisional Patent Application No. 61/100,149 filed Sep. 25, 2008).

As shown in FIG. 1, the present invention provides a method and system for controlling a gas used for anesthesia/analgesia gas delivery, preferably nitrous oxide 10. The low-vacuum fluid is generated by a vacuum source 40 operating to achieve a predetermined parameter. For example, a parameter of the vacuum source 40 is a vacuum strength of 2-20 inches of Hg. In another example, the parameter of the vacuum source 40 is maintaining a scavenging flow rate of at least 45 L/min at the scavenging mask for scavenging excess nitrous oxide. To display the predetermined parameter, one or more monitors 42 may be connected to or integrally formed with the vacuum source 40. The monitors 42 are configured to display said vacuum strength, flow rate, or both of the vacuum source 40.

Another predetermined parameter of the vacuum source 40 is reducing concentration of the nitrous oxide below 25 ppm near the scavenging mask 50. To facilitate the achievement of this parameter, one or more sensors may be configured to display concentration of the nitrous oxide near scavenging mask 50. Note, the predetermined parameter of the vacuum source 30 may be changed depending upon the needs of the patient and the flow rate of nitrous oxide.

The scavenging mask 50 is fluidly connected with the nitrous oxide source 30 and the vacuum source 40. The safety control valve 140 is connected to the fluid connection between the nitrous oxide source 30 and the vacuum source 40. The safety control valve 140 is defaulted to be closed until predetermined parameter of the vacuum source 40 is attained to provide said low-vacuum fluid. If necessary, the safety control valve 140 is configured to provide a user the ability to manually open the safety control valve 140 if necessary. In a further embodiment, the safety control valve 140 is a variable safety control valve configured for adjusting the predetermined parameter for the vacuum source 40 to release the nitrous oxide.

In operation, the safety control valve 140 is configured to be actuated when the low-vacuum fluid is generated by a vacuum source 40 operating at a predetermined parameter is input within the valve 140 to release a flow of the nitrous oxide fluid through the safety control valve 140. The safety control valve 140 is configured to automatically shut off flow of said nitrous oxide when vacuum source 40 is operating below the predetermined parameter. Also, the safety control valve 140 may be configured to automatically shut off flow of the nitrous oxide when flow rate of vacuum source 40 is operating below the flow rate of said nitrous oxide.

Figure 2:
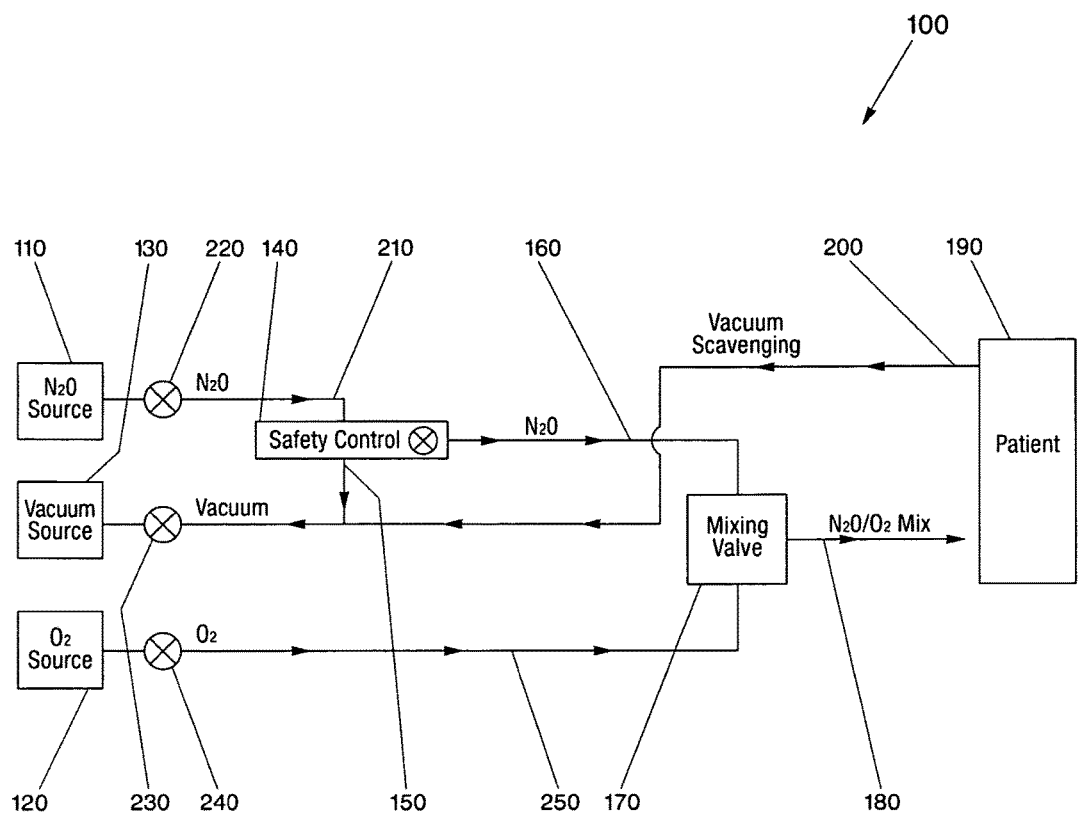
FIG. 2 is a schematic illustration of the nitrous oxide safety system of the present invention.
Figure 3:
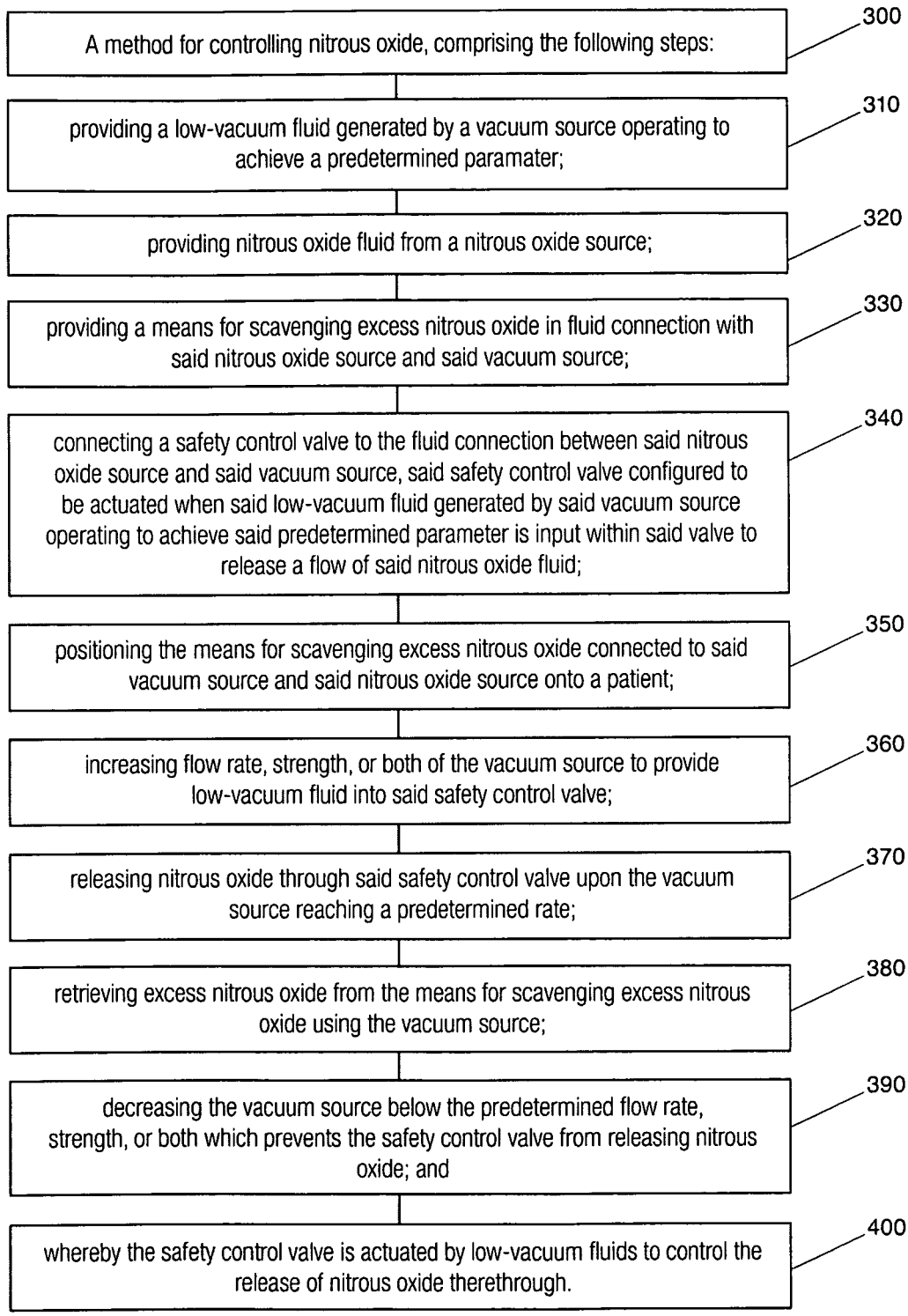
FIG. 3 is a flow chart outlining a method for controlling nitrous oxide of the present invention.

Referring to FIG. 2, a schematic illustration of the nitrous oxide safety system 100 is shown. A fluid, such as nitrous oxide (N2O) used for anesthesia/analgesia gas flows from nitrous oxide source 110 through manual control valve 220 into supply line 210 when valve 220 is open. Note, any type of gas may be used besides nitrous oxide for use in the system or method and preferably gases used for anesthesia/analgesia gas. Next, the nitrous oxide flows to safety control valve 140. In one embodiment, the safety control valve 140 is a pneumatically-actuated or safety control valve. If control valve 140 is open, nitrous oxide flows via supply line 160 into mixing valve 170. Note, the safety control valve 140 may be located before the mixing valve 170 but preferably after mixing valve 170.

Still referring to FIG. 2, a scavenging vacuum or vacuum source is supplied from source 130 and is manually controlled by valve 230. When control valve 230 is open, scavenging suction is applied via line 200 to the patient 190. Scavenging suctions is also applied to safety control valve 140 via branch line 150. In one embodiment, the scavenging suction is applied to the patient by a scavenging means, such as a mask or other means known in the art.

Oxygen flows from oxygen source 120 through manual supply valve 240 into supply line 250 when control valve 240 is open. It should be noted that any type of gas desired may be used other than oxygen for anesthesia gas. Control valves 220, 230, 240 are known in the art are manual valves known in the art. Supply line 250 supplies oxygen ($O_2$) to mixing valve 170 where it mixes with $N_2O$ to a desired ratio and proceeds through a line 180 to patient 190. The desired ratio of the gas mixture is capable of safely sedating a patent during an operatory procedure without causing any harmful effects. Note, mixing valve 170 is any valve known in the art capable of mixing more than one gas to produce a gas mixture.

Safety control valve 140 defaults to the closed position, which prevents through flow of nitrous oxide. The safety control valve 140 remains closed until a vacuum is drawn, via branch line 150, to a pre-selected or predetermined level or parameter. When the vacuum strength reaches this pre-selected or predetermined level or parameter, the safety control valve 140 opens permitting the through flow of nitrous oxide into supply line 160. If the vacuum loses sufficient strength, flow rate, or fails completely, the safety control valve 140 automatically closes stopping the through flow of nitrous oxide.

In operation, the present invention is a used to control the flow of nitrous oxide gas through the safety control valve 140 based upon the strength, flow rate, or both of the vacuum source 130. First, the vacuum source 130 is manually turned on at valve 230. Next, the oxygen source 120 is opened at valve 240 to allow oxygen to flow into the mixing valve 170. Next, the scavenger mask 50 is connected to a patient 190 before or during operatory procedures. The vacuum source 130 is in fluid connection with the scavenger mask 50 to retrieve excess gases. The nitrous oxide source 110 which provides nitrous oxide fluid is manually turned on at valve 220 to allow gas flow from the nitrous oxide source 110, through the valve 220, along the supply line 240 and to the safety control valve 140 where it stops. The nitrous oxide source 110 is in connection with the scavenger mask 50 but cannot be released until the safety control valve 140 allows it to flow.

When the vacuum source 130 reaches a predetermined flow rate and strength, the safety control valve 140 actuates and allows the nitrous oxide fluid to flow through the safety control valve 140 and into the mixing valve 170. It should be noted that in a system with fixed conduit and orifice sizes, flow rate may be proportional to vacuum strength levels. It may be desirable to have minimum critical levels, such as the NIOSH (National Institute for Occupational Safety and Health) recommended flow rate of 45 l/min for the predetermined flow rate for the vacuum source 130 to actuate the safety control valve 140.

Once the safety control valve 140 is actuated by the strength or flow rate of the vacuum source 110, the valve 140 to releases nitrous oxide through the safety control valve 140 and into the mixing valve 170. The nitrous oxide fluid and the oxygen mix within the mixing valve 170 to create a gas mixture. The gas mixture is then delivered into the scavenging mask 50 to sedate the patient 190. At the predetermined flow rate and strength of the vacuum source 130, the vacuum source 130 is retrieving excess gas from the scavenging mask.

Upon a decrease in the flow rate or strength of the vacuum source 130 below the predetermined flow rate and strength, the safety control valve 140 is closed to prevent release of nitrous oxide to the mixing valve 170. In other words, if the vacuum flow rate drops below a certain level, then the nitrous oxide is shut off completely for safety. In one embodiment, the oxygen continues to run despite the safety control valve 140 shutting off the flow of nitrous oxide. To completely shut down the system, the nitrous oxide valve 220, vacuum source valve 230, and the oxygen source valve 240 are manually shut off.

The present invention method also provides a method for controlling nitrous oxide 300 including the following steps. First step 310, a low-vacuum fluid is generated by a vacuum source operating to achieve a predetermined parameter. Second step 320, a nitrous oxide fluid is provided from a nitrous oxide source. Third step 330, a means for scavenging excess nitrous oxide in fluid connection with the nitrous oxide source and the vacuum source is provided. Fourth step 340, a safety control valve or safety control valve is connected to the fluid connection between the nitrous oxide source and the vacuum source. The safety control valve configured to be actuated when the low-vacuum fluid generated by the vacuum source is operating to achieve the predetermined parameter is input within the valve to release a flow of the nitrous oxide fluid. Fifth step 350, the means for scavenging excess nitrous oxide is provided to connect to the vacuum source and said nitrous oxide source onto a patient. Sixth step 360, the flow rate, strength, or both of the vacuum source is increased to provide low-vacuum fluid into said safety control valve. Seventh step 370, nitrous oxide is released through the safety control valve upon the vacuum source reaching a predetermined rate. Eighth step 380, excess nitrous oxide is retrieved from the means for scavenging excess nitrous oxide using the vacuum source. Ninth step 390, the vacuum source is decreased below the predetermined flow rate, strength, or both which prevents the safety control valve from releasing nitrous oxide. Overall, the method for controlling nitrous oxide provides a safety control valve actuated by low-vacuum fluids to control a release of nitrous oxide therethrough 400.

In summary, the present invention provides a method for delivering an anesthesia/analgesia gas, such as nitrous oxide, which eliminates the hazardous situation where anesthesia/analgesia gas could flow without vacuum scavenging systems functioning. The present invention relates to a method or system of controlling anesthesia/analgesia gas delivery which automatically controls its flow relative to the functioning of the vacuum source. The method described herein represents one embodiment of the system but is not intended to exclude the other embodiments described above. In addition, the method and system described above may be used in any type of environment, beyond medical and dental, where a person may come in contact with harmful gases.

Therefore, while there is shown and described herein certain specific structure embodying the invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed is:

1. A system for administering nitrous oxide, comprising:
   a nitrous oxide source having a first control valve;
   a vacuum source having a second control valve;
   a scavenging tube and a nitrous oxide tube fluidly connected to a delivery mask;
   the vacuum source fluidly being connected to the scavenging tube for scavenging excess gases,
   the vacuum source being capable of achieving a predetermined parameter selected from at least one of:
   a predetermined flow rate and a predetermined vacuum strength;
   a variable safety control valve connected to the nitrous oxide source and the vacuum source,
   the variable safety control valve pneumatically actuated when the vacuum source is operating to achieve the predetermined parameter for the vacuum source to release the nitrous oxide,
   the variable safety control valve configured to be in a default closed position to prevent the flow of nitrous oxide from the nitrous oxide source into a delivery mask,
   the variable safety control valve automatically shut off flow of the nitrous oxide when a flow rate of the vacuum source is operating below a flow rate of the nitrous oxide,
   the variable safety control valve pneumatically actuate open to allow the flow of nitrous oxide from the nitrous oxide source to the delivery mask only when the predetermined parameter is achieved;
   wherein the predetermined parameter of the vacuum source is one of:
      a vacuum strength of 2-20 inches of Hg (inch of mercury); and
      a flow rate of at least 45 L/min (Liter per minute).

2. A method for safely administering nitrous oxide to a patient, comprising the following steps:
   providing a fluid generated by a vacuum source, the vacuum source being capable of achieving a predetermined parameter selected from at least one of: a predetermined flow rate and a predetermined vacuum strength;
   providing a nitrous oxide fluid from a nitrous oxide source;
   providing a means for scavenging excess nitrous oxide in fluid connection with said nitrous oxide source and said vacuum source;
   connecting a scavenge system to the nitrous oxide source or the vacuum source a variable safety control valve connected to the nitrous oxide source,
   the variable safety control valve pneumatically actuated when the vacuum source is operating to achieve the predetermined parameter for the vacuum source to release the nitrous oxide,
   the variable safety control valve configured to be in a default closed position to prevent the flow of nitrous oxide from the nitrous oxide source into a delivery mask,
   the variable safety control valve automatically shut off flow of the nitrous oxide when a flow rate of the vacuum source is operating below a flow rate of the nitrous oxide,
   the variable safety control valve pneumatically actuate open to allow the flow of nitrous oxide from the nitrous oxide source to the delivery mask only when the vacuum source is operating to achieve the predetermined parameter;
   increasing flow rate of the vacuum source to provide fluid into the scavenge system;
   releasing nitrous oxide through said scavenge system upon the vacuum source operating to achieve the predetermined parameter;
   whereby the scavenge system is pneumatically actuated by the fluid generated by the vacuum source to control the release of nitrous oxide therethrough;
   wherein the predetermined parameter of the vacuum source is one of:
      a vacuum strength of 2-20 inches of Hg (inch of mercury); and
      a flow rate of at least 45 L/min (Liter per minute).

* * * * *